United States Patent [19]

Katz et al.

[11] 4,213,464
[45] Jul. 22, 1980

[54] TRANSDUCER ASSEMBLY

[75] Inventors: Louis Katz, Flushing; Kurt W. Weil, New York, both of N.Y.

[73] Assignee: Sonometrics Systems, Inc., New York, N.Y.

[21] Appl. No.: 867,675

[22] Filed: Jan. 9, 1978

[51] Int. Cl.$^2$ .............................................. A61B 3/16
[52] U.S. Cl. .................................. 128/645; 128/646; 128/652; 128/745; 248/430
[58] Field of Search ............ 128/2 T, 2 V, 652, 660, 128/745, 645, 646; 248/1, 424, 429, 430, 475 B, 548; 73/80; 308/6 R

[56] References Cited

U.S. PATENT DOCUMENTS

| | | | |
|---|---|---|---|
| 2,579,599 | 12/1951 | Moroney | 248/430 |
| 3,299,882 | 1/1967 | Masino | 73/80 X |
| 3,390,572 | 7/1968 | Murr | 73/80 |
| 3,453,998 | 7/1969 | Giglio | 128/2 T |

*Primary Examiner*—Richard T. Stouffer
*Attorney, Agent, or Firm*—McAulay, Fields, Fisher & Goldstein

[57] ABSTRACT

A transducer assembly is provided for moving a transducer into operative contact with a human eye. The assembly comprises a transducer holder that receives a transducer therein. A slide supports the transducer holder for rearward movement from a home position. A spring normally biases the transducer holder to the home position. Thus, as the assembly is moved toward the eye and the transducer engages the eye, the slide moves rearwardly against the spring bias to maintain the transducer against the eye of the patient. In order to prevent undue force on the eye, a release device is provided between the transducer holder and the transducer and is responsive to a preselected value of force for releasing the transducer from the transducer holder.

13 Claims, 6 Drawing Figures

U.S. Patent  Jul. 22, 1980  4,213,464
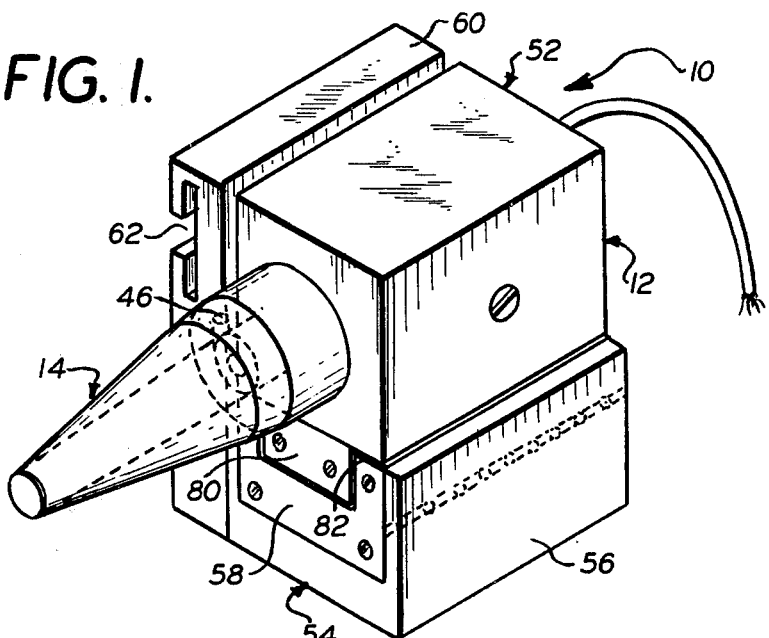
FIG. 1.
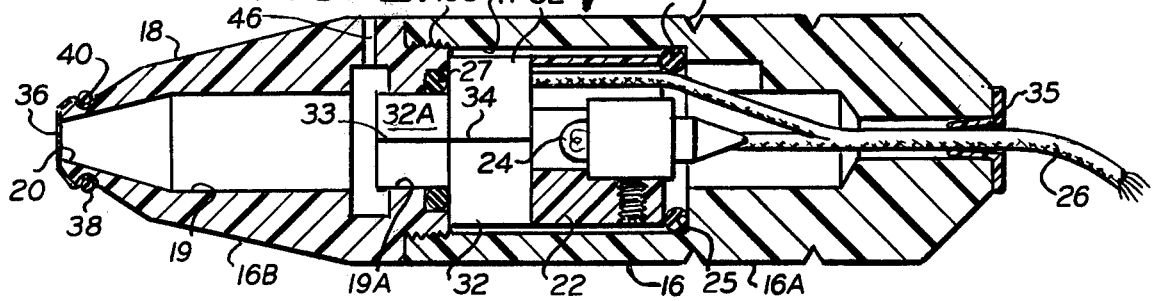
FIG. 2.
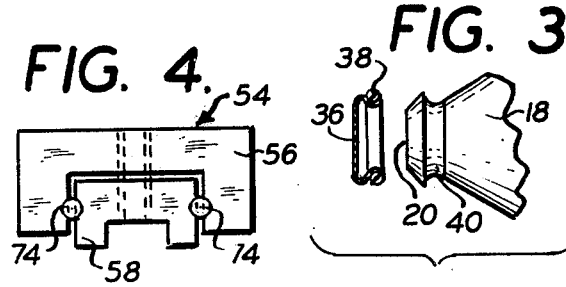
FIG. 4.  FIG. 3.
FIG. 5.
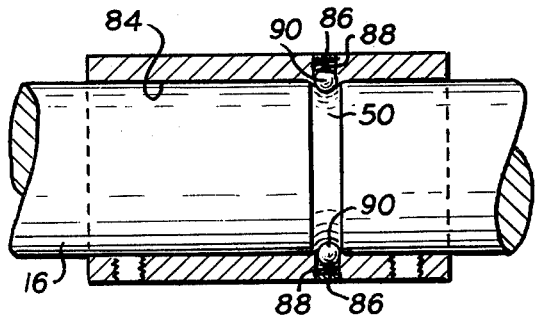
FIG. 6.
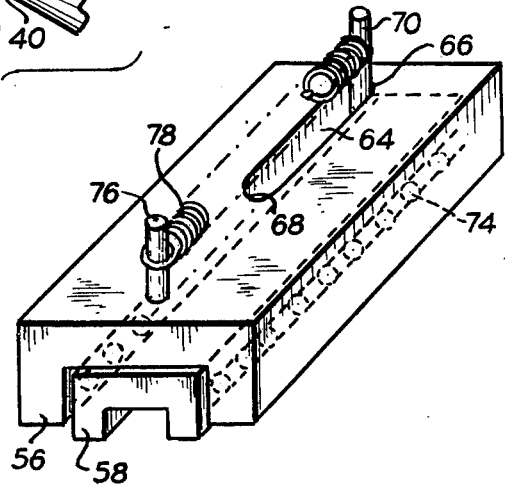

TRANSDUCER ASSEMBLY

BACKGROUND OF THE INVENTION

This invention relates generally to a transducer assembly and, more particularly, pertains to a transducer assembly for minimizing the application of forces on the human eye when the transducer is moved into contact therewith.

During the measurement of various parameters of the eye, an instrument or probe must be moved into contact with the cornea of the eye. However, in many applications it is imperative that the probe does not exert any force which would deform the pliable covering of the eye. In addition, if damage to the eye is to be prevented, excessive force against the eye by the probe must be avoided. At present, there is commercially available apparatus that is operable to engage the eye with a measured force. However, these devices suffer from severe drawbacks.

For example, one such device includes a slide member that holds an optical device. The slide member is connected to the upper end of a fulcrum bar that is pivotally connected at its opposite end to a stationary member. An adjustable spring bears against the opposite end so that as the slide is moved rearwardly, the spring is compressed by the bar thereby producing a measured reaction force against the slide. This type of apparatus suffers from excessive friction in view of the number of operating parts in addition to the fact that the amount of spring bias is adjusted by a movable set screw and therefore is extremely inaccurate.

Of even greater importance is the fact that when the slide reaches the end of its travel, further movement of the optical device toward the eye will cause a force to be exerted on the eye which might very well damage the eye. In other words, there is no safety device that would limit the maximum amount of force that would be placed on the eye.

Accordingly, an object of the present invention is to provide an improved transducer assembly for limiting the force applied to the eye by a transducer.

A more specific object of the present invention is to provide a transducer assembly which prevents undue forces due, for example, to operator error or patient movement from being applied to the eye.

A further object of the present invention resides in the novel details of construction that provide a transducer assembly of the type described wherein excessive force on the eye is eliminated.

A further object of the invention is the provision of a transducer assembly in which the transducer section may be easily and quickly assembled.

Another object of the invention is the provision of an improved transducer construction.

SUMMARY OF THE INVENTION

Accordingly, a transducer assembly constructed according to the present invention is utilized to limit the force that a transducer applies to a human eye, and comprises a transducer holder. The transducer is received in the holder and a slide supports the transducer holder for rearward movement from a home position. Biasing means biases the transducer holder to the home position and release means is provided between the transducer holder and the transducer and is responsive to a preselected value of force for releasing the transducer from the transducer holder.

BRIEF DESCRIPTION OF THE DRAWINGS

Other features and advantages of the present invention will become more apparent from a consideration of the following detailed description, when taken in conjunction with the accompanying drawings, in which:

FIG. 1 is a perspective view of a transducer assembly constructed according to the present invention;

FIG. 2 is a vertical sectional view of the transducer portion of the transducer assembly;

FIG. 3 is a detailed sectional exploded view, to enlarged scale, of the membrane and transducer housing portion of the assembly;

FIG. 4 is a front view of the slide arrangement of the assembly of the present invention;

FIG. 5 is a bottom plan view of the slide arrangement; and,

FIG. 6 is a vertical sectional view showing the relationship between the holder and the transducer.

DESCRIPTION OF THE PREFERRED EMBODIMENT

Accordingly, a transducer assembly constructed according to the present invention is designated generally by the reference character 10 in FIG. 1 and comprises a transducer carriage 12 and a transducer apparatus 14 that is supported by the carriage. The transducer apparatus 14 is shown more specifically in FIGS. 2 and 3 and comprises a hollow tubular member 16 having a rear section 16A and a front section 16B in the form of a truncated cone 18 having a central chamber 19, the front end of which is in the shape of a truncated cone, and an open front end 20. The sections 16A and 16B are threadedly connected together at 16C. The section 16B is provided with a central enlarged diameter passage 17 that receives a circular support 22 for a lamp 24. A set screw 21 adjusts the position of the lamp with respect to the support 22 so that the lamp can be accurately adjusted to be coaxial with the section 16A. An O-ring 23 is positioned between the rear surface of the support 22 and a shelf 25 formed within the passage 17.

Also received within the passage 17 forwardly of the lamp 24 is a transducer unit 32 which may comprise a piezoelectric crystal and matching network that is resonant at the desired frequency. In practice, the crystal is resonant at 15 MHz. The unit 32 is provided with a reduced diameter front portion 32A that is slidingly received in a rear portion 19A of the chamber 19. An O-ring 27 is received between the unit 32 and the section 16B to provide a fluid-tight seal therebetween. The crystal is positioned so that it is coaxial in its own housing and, in turn, with the member 16.

Additionally, an axial through bore 34 is provided in the unit 32. Received within the bore is a fibre optic bundle 33. The bundle 33 brings the lamp 24 to the front surface of the unit 32 to facilitate fixation by the patient. That is, the lamp 24 is a fixation light that aids in aligning the transducer with the line of sight of the patient. By sighting the axially positioned lamp, the patient automatically aligns his line of sight with the transducer unit. The fibre bundle eliminates problems encountered previously wherein the patient was required to sight the lamp by looking down the bore 34. The long narrow diameter bore made it very difficult for the patient to fixate on the lamp.

A single cable 26 connects to both the transducer unit 32 and the lamp 24 and serves to apply the necessary signal energy to these elements. The cable exits through the rear of the section 16A through a suitable strain relief 35.

A removable and interchangeable membrane 36 seals the opening 20 and, in effect, defines the other end wall of the conical chamber. More specifically, the membrane 36, which may be fabricated from a resilient material such a 1 mil silicon rubber or the like, is sealed to an O-ring 38 along its peripheral edge. It is preferable that the speed of sound in the membrane be the same as the speed of sound through water and that the membrane be transparent to light. Additionally, the front end 18 of the member 16 is provided with an annular groove 40 that is located adjacent the open end 20. This arrangement permits the easy and quick connection and removal of the membrane with the member 16 since it is preferable that a new membrane be used for each patient. Thus, the membrane 36 may be placed against the finger or an appropriate tool with the O-ring 38 facing outwardly. The O-ring is then pushed on to the tapered end of the member 16 and moved rearwardly until it is engaged in the annular groove 40. The O-ring will remain in the groove, thereby retaining the membrane in place. This construction also produces a uniform tension in the membrane.

A radially extending bore 46 communicates with the chamber 19 and provides a passage for the flow of a fluid into the chamber. In practice, when the transducer assembly is operated, water is introduced into the chamber 19 to provide a sound coupling path between the transducer unit and the eye of the patient. More specifically, the water is injected into the chamber by a hypodermic syringe. The diameter of the bore 46 is selected to be slightly larger than the diameter of the hypodermic needle so that air can exit through the space between the needle and the bore wall as the water enters the chamber.

An annular groove 50 is provided on the member 16A adjacent the rear end thereof for purposes which will become apparent from a consideration of the description of the holder section of the transducer assembly set forth hereinbelow.

The transducer carriage 12 generally comprises a transducer holder 52 and a slide 54 which comprises a stationary member 56 and a sliding member 58. The slide 54 is shown more particularly in FIGS. 1, 4, and 5 and, as noted above, includes a channel shaped stationary member 56. Connected to one side of the stationary member 56 is an upstanding wall 60 having a T-slot 62 in the outer surface thereof. The T-slot is adapted to mate with a T-shaped member on an appropriate machine so that the transducer assembly of the present invention may be mounted on the machine. Received in the bottom wall of the member 56 is an elongated longitudinally extending slot 64 having end walls 66 and 68. A depending pin 70 extends downwardly from the lower surface of the bottom wall of the member 56 and is positioned adjacent a front surface 72 thereof.

The sliding member 58 is similarly channel shaped and is received within the channel of the member 56, as shown in FIG. 4. Ball bearing supports 74 are received in appropriate races in the sidewall of the sliding member 58 and the inner wall of the upstanding legs of the stationary member 56 to support the sliding member 58 in substantially a frictionless engagement.

Depending from the bottom wall of the sliding member 58 is a pin 76 that is received in the elongated slot 64. A spring 78 is connected between the pin 76 and the pin 70 on the stationary member 56. The end walls 66 and 68 of the slot are adapted to engage the pin 76 to limit the movement of the sliding member 58. The spring 78 biases the sliding member forwardly to an orientation wherein the pin 76 engages the front wall 68 of the slot 64. This is the normal or home position of the sliding member. However, the sliding member 58 may be moved rearwardly relative to the stationary member 56 until the pin 76 engages the rear wall 66 of the elongated slot.

The transducer holder 52 is provided with a depending tang 80 that fits within the channel of the sliding member 58. The transducer holder and the sliding member 58 are rigidly connected together by any conventional means such as screws or the like. The holder 52 is provided with shoulders 82 which seat on the upper edges of the upstanding legs of the sliding member 58 to further stabilize the construction.

As shown in FIG. 6, the transducer holder 52 is provided with an axial through bore 84 which receives the rear portion of the transducer housing 16 therein. Provided within the wall defining the bore 84 are radially extending holes 86 that receive respective springs 88 therein. Received on the springs 88 are respective balls 90. The openings to the holes 86 may be peened over or otherwise deformed so that the balls are retained within the openings to the holes and only a portion of the balls project into the bore 84. The balls 90 are adapted to extend into the annular groove 50 in the tubular member 16A to releasably retain the transducer apparatus in position.

In operation, the transducer is inserted into the bore 84 in the transducer holder until the balls 90 project into the recess 50 so that the transducer assembly is retained in place in the holder. The transducer assembly is then mounted on the associated machine such as a slit-lamp stand or the like and the chamber 30 is filled with a fluid such as water. The lamp 24 is illuminated and the machine such as the aforementioned slit-stand is operated so that the assembly is moved forwardly until the membrane 36 engages the cornea of the patient. Further forward movement of the transducer assembly will cause rearward movement of the holder 52 relative to the stationary member 56. Accordingly, when the operator observes such movement, he may cease forward movement of the transducer assembly. The force constant of the spring is selected so that an appropriate force will now be exerted on the cornea that will maintain the membrane in contact with the eye and yet eliminate deformation of the eye to prevent erroneous results. That is, since the spring 78 is connected with the pin 76 on the sliding member 58 which, in turn, is rigidly secured to the transducer holder 52, the spring 78 effectively biases the transducer apparatus into contact with the eye. In practice, a spring constant is chosen so that a force of approximately 7 grams will be produced when the spring is extended 1.5 mm. In other words, the spring will have a force constant of 4.66 grams/mm.

Assuming, for some reason, that the assembly is continuously moved forward, the pin 76 will engage the rear wall 66 of the slot 64 to terminate further rearward movement of the holder 52. Under normal circumstances, therefore, further forward movement of the transducer assembly will cause the transducer apparatus to bear against the eyeball and may cause great damage.

On the other hand, in the present invention the force on the transducer assembly will simply cause the balls 90 to ride back into the holes 86 against the bias of the springs 88. Accordingly, once the balls 90 clear the annular groove 50, the transducer apparatus will simply move rearwardly with respect to the holder 52 thereby releasing the pressure on the eye. The force constant of the springs 86 is such that the balls 90 will be depressed long before any appreciable force that would cause any damage to the eye is generated by the assembly.

Accordingly, a transducer assembly has been disclosed that provides an efficient manner of moving a measuring device into contact with a human eye and eliminates the possibility of eye damage due to forces applied to the eye.

While a preferred embodiment of the invention has been shown and described herein it will become obvious that numerous omissions, changes and additions may be made in such embodiment without departing from the spirit and scope of the present invention.

What is claimed is:

1. A transducer assembly for moving a transducer into operative contact with a human eye, comprising:
   (a) a transducer holder;
   (b) a transducer received in said holder;
   (c) a slide for supporting said transducer holder for rearward movement from a home position;
   (d) biasing means for biasing said transducer holder to said home position; and
   (e) complementary formed release means between said transducer holder and said transducer for normally releasably connecting together said transducer and said transducer holder and being responsive to a preselected value of force within the normal operating range of said release means for releasing said transducer from said transducer holder.

2. A transducer assembly as in claim 1, in which said release means comprises an annular recess on one of said transducer and transducer holder, and a spring biased member on the other of said transducer and transducer holder engageable in said annular recess for releasably connecting said transducer with said transducer holder.

3. A transducer assembly as in claim 1, in which said transducer comprises a transducer housing, a transducer unit within said housing, said housing having a front opening, a membrane covering said opening, and complementary formed connecting means for connecting said membrane to said housing.

4. A transducer assembly as in claim 3, in which said transducer unit is coaxial with said housing, an axial bore in said unit, a fibre optic bundle received in said axial bore, and a lamp positioned behind said transducer to illuminate said fibre optic bundle.

5. A transducer assembly as in claim 3, in which said connecting means comprises an annular groove in said housing adjacent said front opening, and an O-ring connected to the outer edge of said membrane and received in said annular groove.

6. A transducer assembly as in claim 1, in which said slide comprises a stationary member adapted to be connected to an associated device, a slidable member on said stationary member affixed to said transducer holder, and stop means for limiting rearward travel of said slidable member relative to said stationary member.

7. A transducer assembly as in claim 6, in which stop means comprises an elongated slot in said stationary member, and a pin depending from said slidable member and received in said slot, whereby engagement of said pin with the rear wall of said slot limits the rearward movement of said transducer holder.

8. A transducer assembly as in claim 7, in which said biasing means comprises a spring connected between said pin and said stationary member.

9. A transducer assembly as in claim 8, in which said spring has a spring constant of substantially 4.66 gm/mm.

10. A carriage for movably supporting a device adapted to be moved into operative engagement with the human eye, comprising:
    a holder for supporting the device;
    releasable retaining means on said holder engagable with complementary formed means on the device for normally retaining the device in position and being responsive to a preselected value of force within the normal operating range of said release means for releasing the device to permit relative movement between the device and said holder;
    a slide for supporting said holder for rearward movement from a home position; and
    biasing means for biasing said slide toward said home position.

11. A carriage as in claim 10, in which said slide comprises a base, said base having a bottom wall and a longitudinally extending channel, a longitudinally extending slot in said bottom wall, a member slidably received in said channel and connected to said holder, a pin depending from said member and slidably received in said slot, said pin being engagable with the front wall defining said slot to position said holder in said home position, and said pin being engageable with the rear wall defining said slot to limit rearward movement of said holder.

12. A carriage as in claim 10, in which said biasing means comprises a spring connected between said pin and said base.

13. A carriage as in claim 10, in which said holder comprises a through bore adapted to receive said device therethrough, and said releasable retaining means comprises a spring biased member projecting into said bore and adapted to be received in a recess in the device, whereby movement of the device in a direction transverse to the biasing force on said spring biased member causes said member to retract to permit unrestricted movement of the device.

* * * * *